United States Patent
Kakee (10) Patent No.: US 8,425,419 B2
(45) Date of Patent: Apr. 23, 2013

(54) ULTRASONIC DIAGNOSTIC APPARATUS AND ULTRASONIC DIAGNOSTIC METHOD

(75) Inventor: Akihiro Kakee, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 906 days.

(21) Appl. No.: 12/237,694

(22) Filed: Sep. 25, 2008

(65) Prior Publication Data

US 2009/0082669 A1 Mar. 26, 2009

(30) Foreign Application Priority Data

Sep. 26, 2007 (JP) ................................. 2007-250295

(51) Int. Cl.
*A61B 8/00* (2006.01)

(52) U.S. Cl.
USPC .......................................... 600/437; 600/407

(58) Field of Classification Search .................. 600/437, 600/407; 382/128, 203, 189
See application file for complete search history.

(56) References Cited

U.S. PATENT DOCUMENTS

| | | | |
|---|---|---|---|
| 6,398,733 B1 | 6/2002 | Simopoulos et al. | |
| 6,475,148 B1 * | 11/2002 | Jackson et al. | 600/439 |
| 2003/0158479 A1 * | 8/2003 | Li et al. | 600/437 |
| 2004/0260180 A1 * | 12/2004 | Kanai et al. | 600/449 |
| 2005/0201600 A1 * | 9/2005 | Takarada | 382/128 |
| 2006/0056655 A1 * | 3/2006 | Wen et al. | 382/103 |

FOREIGN PATENT DOCUMENTS

| | | |
|---|---|---|
| JP | 2002-125971 | 5/2002 |
| JP | 2004-159770 | 6/2004 |
| JP | 2005-177336 | 7/2005 |
| JP | 2005-305129 | 11/2005 |
| JP | 2005-319296 | 11/2005 |
| JP | 2006-55672 | 3/2006 |

OTHER PUBLICATIONS

Japanese Office Action mailed Apr. 24, 2012, in Japanese Patent Application No. 2007-250295 filed Sep. 26, 2007 (with English Translation).

* cited by examiner

*Primary Examiner* — Tse Chen
*Assistant Examiner* — Joel F Brutus
(74) *Attorney, Agent, or Firm* — Oblon, Spivak, McClelland, Maier & Neustadt, L.L.P.

(57) ABSTRACT

The average value of sensitivities in each of the image areas (m×n) recognized as a subject is calculated. If the average value of sensitivities is greater than the threshold value, the transmission voltage to the ultrasonic probe is limited according to the difference between the average value of sensitivities and the threshold value.

11 Claims, 4 Drawing Sheets

ULTRASONIC DIAGNOSTIC APPARATUS AND ULTRASONIC DIAGNOSTIC METHOD

CROSS-REFERENCE TO RELATED APPLICATIONS

This application is based upon and claims the benefit of priority from prior Japanese Patent Application No. 2007-250295, filed Sep. 26, 2007, the entire contents of which are incorporated herein by reference.

BACKGROUND OF THE INVENTION

1. Field of the Invention

This invention relates to an ultrasonic diagnostic apparatus which transmits an ultrasonic beam from an ultrasonic probe to a subject, such as a biological body, receives the echoes from the subject, and obtains ultrasonic image data on the subject, and more particularly to an ultrasonic diagnostic apparatus and an ultrasonic diagnostic method which adjust a transmission voltage sent to an ultrasonic probe to the optimum value.

2. Description of the Related Art

With an ultrasonic diagnostic apparatus, an ultrasonic probe is brought into contact with a subject, such as a biological body. In this state, the ultrasonic probe transmits an ultrasonic beam to the inside of the subject and receives the echoes from the inside of the subject, thereby acquiring ultrasonic image data on the subject. The ultrasonic probe transmits an ultrasonic beam of acoustic power corresponding to a transmission voltage specified by a system control unit of the ultrasonic diagnostic apparatus. As for the transmission voltage to the ultrasonic probe, a transmission voltage preset within an acoustic power limit range by the system control unit is set as the maximum transmission voltage.

The ultrasonic beam is adjusted according to the type of subject, such as an unborn baby or an internal organ, so as not to transmit high acoustic power to the subject. The acoustic power of the ultrasonic beam is adjusted by the user manually operating an acoustic power adjustment switch provided on the panel of the ultrasonic diagnostic apparatus. The acoustic power adjustment of the ultrasonic beam is made in the acoustic power limit range by the manual operation, with the transmission voltage calculated by the system control unit being used as the maximum transmission voltage.

In the ultrasonic diagnostic apparatus, too, the safety of acoustic power of an ultrasonic beam is required. The transmission voltage for the ultrasonic beam is set to a transmission voltage calculated in advance by the system control unit. Accordingly, when an actual subject is diagnosed, the acoustic power of the ultrasonic beam has to be limited for the region which needs no diagnosis in the subject. To limit the acoustic power of the ultrasonic beam, the user operates the acoustic power adjustment switch manually, thereby adjusting the acoustic power of the ultrasonic beam to the optimum value. Such an adjustment of the acoustic power of the ultrasonic beam is made for, for example, each of a plurality of diagnostic regions of the subject.

However, when the user operates the acoustic power adjustment switch manually for each of the plurality of diagnostic regions to optimize the acoustic power of the ultrasonic beam, this decreases the diagnostic throughput of the diagnostic regions. Moreover, since a plurality of diagnostic regions of the subject are diagnosed, the total time required for the diagnostic regions becomes longer. Consequently, the irradiation time of the ultrasonic beam to the subject becomes longer.

The technique for not only controlling a method of driving a plurality of piezoelectric vibrators included in an ultrasonic probe in an ultrasonic Doppler spectrum method so as to follow the heat generation limit or acoustic output limit but also observing the Doppler spectrum with high sensitivity has been disclosed in Jpn. Pat. Appln. KOKAI Publication No. 2005-305129. Specifically, Jpn. Pat. Appln. KOKAI Publication No. 2005-305129 has disclosed a method of switching between a power mode in which the amplitudes of the driving signals corresponding to a plurality of piezoelectric vibrators are relatively high and a power mode in which the amplitudes of the driving signals are relatively low in synchronization with the biological signal of the subject.

It is an object of the invention to provide an ultrasonic diagnostic apparatus and an ultrasonic diagnostic method which are capable of adjusting a transmission voltage sent to an ultrasonic probe according to a subject to an optimum value automatically.

BRIEF SUMMARY OF THE INVENTION

According to a first aspect of the invention, there is provided an ultrasonic diagnostic apparatus comprising: an ultrasonic probe; a transmitting and receiving unit which transmits a voltage to the ultrasonic probe to cause the ultrasonic probe to transmit an ultrasonic beam and receives an echo from a subject with the ultrasonic probe; a signal processing unit which acquires ultrasonic image data on the subject from an output signal of the transmitting and receiving unit; a subject recognition unit which recognizes an image area corresponding to the subject from the ultrasonic image data; and an optimum voltage computing unit which limits the transmission voltage to the ultrasonic probe on the basis of a sensitivity in the image area recognized as the subject by the subject recognition unit and a preset threshold value.

According to a second aspect of the invention, there is provided an ultrasonic diagnostic method comprising: transmitting a voltage to an ultrasonic probe to cause the ultrasonic probe to transmit an ultrasonic beam; receiving an echo from a subject with the ultrasonic probe; acquiring ultrasonic image data on the subject from an output signal of the ultrasonic probe; recognizing an image area corresponding to the subject from the ultrasonic image data; and limiting the transmission voltage to the ultrasonic probe on the basis of a sensitivity in the image area recognized as the subject and a preset threshold value.

DETAILED DESCRIPTION OF THE INVENTION

Hereinafter, referring to the accompanying drawings, an embodiment of the invention will be explained.

Figure 1:
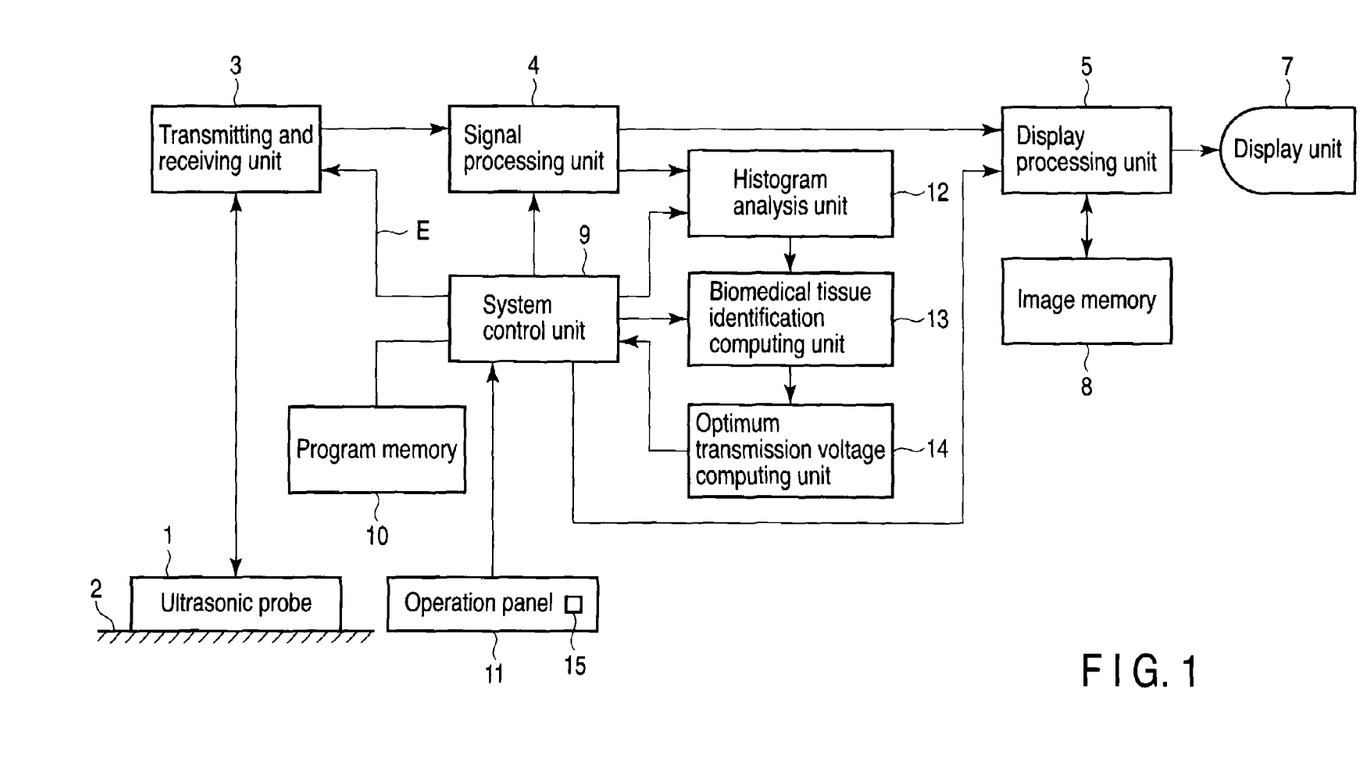
FIG. 1 is a block diagram showing the configuration of an ultrasonic diagnostic apparatus according to an embodiment of the invention.

FIG. 1 shows the configuration of an ultrasonic diagnostic apparatus according to an embodiment of the invention. An ultrasonic probe 1 has a plurality of vibrators. The ultrasonic probe 1 makes contact with a subject 2, such as a biological body. In this state, the ultrasonic probe 1 transmits an ultrasonic beam to the inside of the subject 2, receives the reflected wave from, for example, a target region in the subject 2, and outputs its echo signal. The ultrasonic probe 1 is connected to a transmitting and receiving unit 3.

The transmitting and receiving unit 3 applies a transmission voltage E of a specific transmission waveform to the individual vibrators of the ultrasonic probe 1 in such a manner that there is a delay between the vibrators, thereby performing a scan with the ultrasonic beam transmitted from the ultrasonic probe 1. At the same time, the transmitting and receiving unit 3 receives the reflected wave from the subject 1 and adds the echo signals output from the individual vibrators by introducing a delay in receiving. The output signal of the transmitting and receiving unit 3 is input to a signal processing unit 4.

The signal processing unit 4 subjects the output signal of the transmitting and receiving unit 3 to various processes, including a gain process, a phase detection process, a low-pass filter (LPF) process, an compression process (LOG), and an image filtering process and outputs the result of these processes as subject data. The signal processing unit 4 outputs the subject data consecutively each time, for example, the ultrasonic probe 1 does a scan with the ultrasonic beam. The subject data output from the signal processing unit 4 is composed of a plurality of pixels each having a luminance value. When the subject 2 is a biological body, the subject data output from the signal processing unit 4 is referred to as biological data.

The output data of the signal processing unit 4 is input to a display processing unit 5. On the basis of the output data, the display processing unit 5 constructs either two- or three-dimensional image data or both, subjects the image data to a post-process, such as a dynamic range process, and displays either two- or three-dimensional ultrasonic image data or both on a display unit 7. An image memory 8 is connected to the display processing unit 5. The display processing unit 5 stores either the constructed two- or three-dimensional ultrasonic image data or both in the image memory 8.

The display unit 7 is composed of, for example, a liquid-crystal display.

A system control unit 9 is composed of a CPU. A program memory 10 and an operation panel 11 are connected to the system control unit 9. In the program memory 10, a control program for the ultrasonic diagnostic apparatus is stored in advance. The system control unit 9 executes the control program stored in the program memory 10, thereby giving an operation control instruction to each of the transmitting and receiving unit 3, signal processing unit 4, display processing unit 5, a histogram analysis unit 12, a biomedical tissue identification computing unit 13, and an optimum transmission voltage computing unit 14.

When the control program for the ultrasonic diagnostic apparatus transmits a voltage to the ultrasonic probe 1 to cause the probe 1 to transmit an ultrasonic beam, receives the echo from the subject 2 with the ultrasonic probe 1, and obtains ultrasonic image data on the subject 2, the control program causes the probe to recognize an image area corresponding to the subject 2 in the ultrasonic image data and limits a transmission voltage E to the ultrasonic probe 1 on the basis of the sensitivity in at least the recognized image area and a preset threshold value.

The operation panel 11 is provided with various switches for operating the apparatus. The operation panel 11 is further provided with an acoustic power adjustment switch 15 for manual operation. The acoustic power adjustment switch 15, when being operated manually, gives an instruction to optimize the transmission voltage E to the ultrasonic probe 1 to the system control unit 9.

Figure 3:
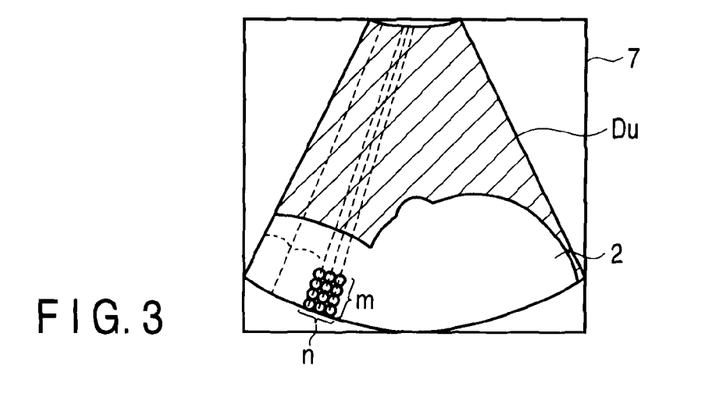
FIG. 3 shows an ultrasonic image of a subject, such as an unborn baby, displayed on a display unit of the apparatus of the embodiment.

The subject data, or the ultrasonic image data, output from the signal processing unit 4 is input to the histogram analysis unit 12. As shown in FIG. 3, the histogram analysis unit 12 sets samples m (e.g., the numbers of pixels) in the ultrasonic image data in the direction of depth in which the ultrasonic probe 1 transmits an ultrasonic beam to the inside of the subject 2. At the same time, the histogram analysis unit 12 sets rasters n (e.g., the number of pixels) in the scanning direction of the ultrasonic beam. Then, the histogram analysis unit 12 sets a plurality of image areas each composed of samples m and rasters n (m×n pixels). One image area (m×n) is, for example, 4×4 pixels.

The histogram analysis unit 12 calculates a variance value $V_i$ of each luminance value in the subject data output from the signal processing unit 4 for each image area (m×n) and further calculates an average value $S_i$ by performing an averaging process (LPF) of the individual luminance values in the output data of the signal processing unit 4 for each image area (m×n).

The output data from the signal processing unit 4 with the transmission voltage E to the ultrasonic probe 1 being off is input to the histogram analysis unit 12, which collects the output data as noise data. The noise data may be stored in advance in an external storage device or the like. In this case, the noise data is read from the external storage device by the system control unit 9 and is supplied to the histogram analysis unit 12. The histogram analysis unit 12 calculates an average value $N_i$ by performing the averaging process (LPF) of the individual luminance values in the noise data for each image area (m×n).

The biomedical tissue identification computing unit 13 receives the variance value $V_i$ of luminance values, average value $S_i$, and average value $N_i$ of the noise data for each image area (m×n) in the subject data obtained by the histogram analysis unit 12. The biomedical tissue identification computing unit 13 determines for each of the image areas (m×n) whether the image area is the subject 2, on the basis of the variance value $V_i$, average value $S_i$, and average value $N_i$.

Specifically, the biomedical tissue identification computing unit 13 calculates the difference $SNR_i$ between the average value $S_i$ of the subject data and the average value $N_i$ of the noise data:

$$SNR_i = S_i - N_i \qquad (1)$$

Let the difference $SNR_i$ be a sensitivity.

The biomedical tissue identification computing unit 13 determines for each image area (m×n) whether the image area is the subject 2, on the basis of the variance value $V_i$ of the subject data and the sensitivity $SNR_i$. The conditions for determining whether the image area is the subject 2 are:

$$SNR_i > SNR_{min} \qquad (2)$$

$$V_{min} < V_i < V_{max} \qquad (3)$$

where $SNR_{min}$, $V_{min}$, and $V_{max}$ are values to be set in advance.

The optimum transmission voltage computing unit 14 limits a transmission voltage E to the ultrasonic probe 1 on the basis of the sensitivity SNRi of each of the image areas (m×n) recognized as the subject 2 by the biomedical tissue identification computing unit 13 and a preset threshold value SNRtarget. Specifically, the optimum transmission voltage computing unit 14 calculates the average value SNRmean of sensitivities SNRi in each of the image areas (m×n). The SNRmean of sensitivities SNRi is a signal-to-noise ratio in each of the image areas (m×n) recognized as the subject 2.

The optimum transmission voltage computing unit 14 compares the average value SNRmean of sensitivities with the threshold value SNRtarget. If the comparison of the average value SNRmean of sensitivities with the threshold value SNRtarget has shown that the average value SNRmean of sensitivities SNRi is greater than the threshold value SNRtarget, the optimum transmission voltage computing unit 14 calculates a transmission voltage E=Ea−ΔE lower than the transmission voltage E to the ultrasonic probe 2 by a voltage value ΔE corresponding to the difference between the sensitivity average value SNRmin and the threshold value SNRtarget and sends the resulting transmission voltage E to the system control unit 9. Ea is a transmission voltage immediately before the transmission voltage is lowered by the voltage value ΔE.

The system control unit 9 receives the transmission voltage E (=Ea−ΔE) found by the optimum transmission voltage computing unit 14 and feeds back the transmission voltage E to the transmitting and receiving unit 3.

Furthermore, when having received an instruction to optimize the transmission voltage E to the ultrasonic probe 1 from the acoustic power adjustment switch 15, the system control unit 9 issues an operation control instruction to each of the histogram analysis unit 12, biomedical tissue identification computing unit 13, and optimum transmission voltage computing unit 14 and performs the following control as described above.

Specifically, the optimum transmission voltage computing unit 14 compares the average value SNRmean of sensitivities with the threshold value SNRtarget. If the comparison has shown that the average value SNRmean of sensitivities SNRi is greater than the threshold value SNRtarget, the system control unit 9 calculates a transmission voltage E=Ea−ΔE lower than the transmission voltage E to the ultrasonic probe 1 by a voltage value ΔE corresponding to the difference between the average value SNRmin of sensitivities and the threshold value SNRtarget and sends the resulting transmission voltage E to the system control unit 9. The system control unit 9 is set so as to control the transmission voltage E to the ultrasonic probe 1 to keep the voltage E in the acoustic power limit range.

Figure 2:
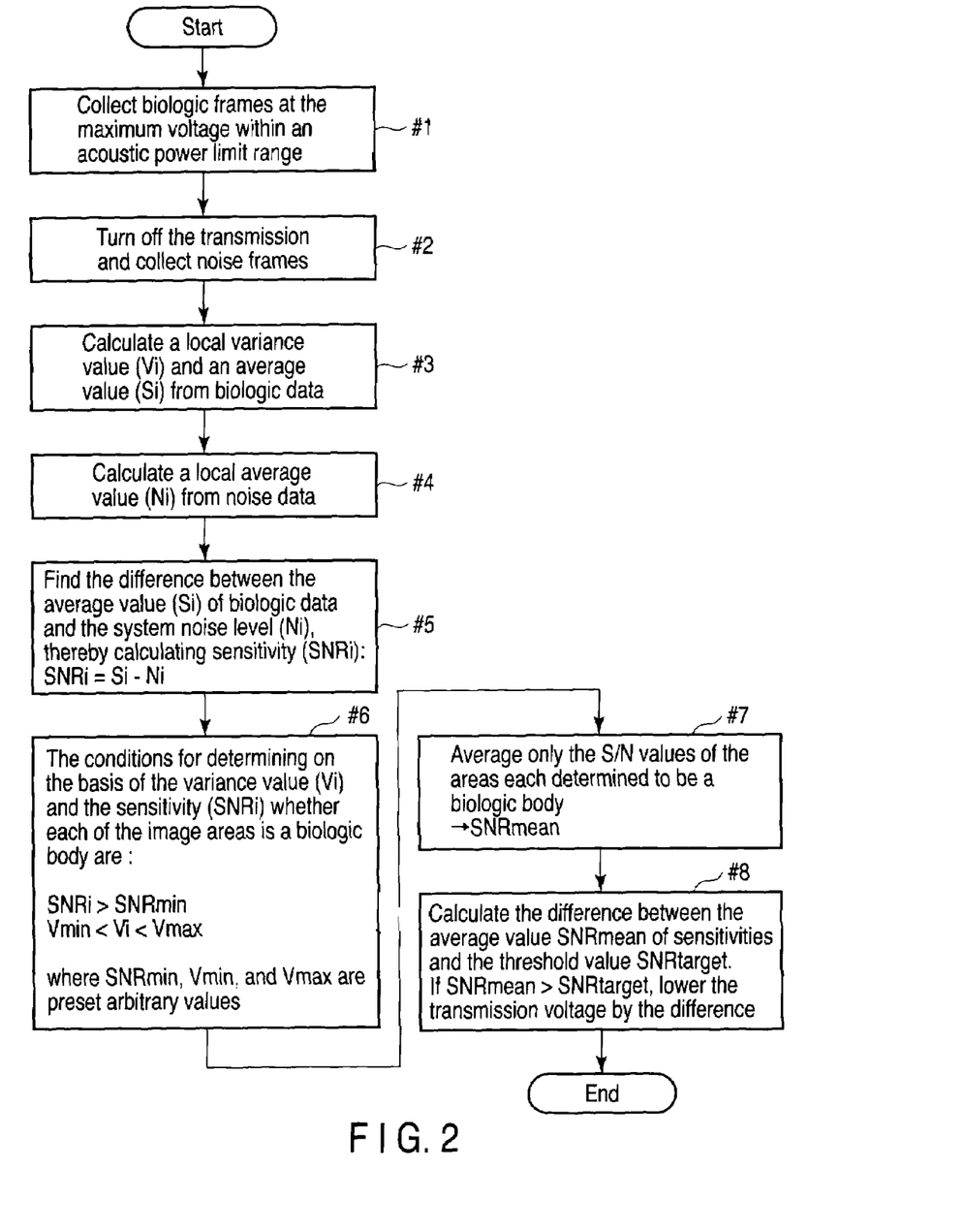
FIG. 2 is a flowchart to help explain the optimization of a transmission voltage in the apparatus of the embodiment.

Next, the operation of adjusting the transmission voltage E sent to the ultrasonic probe 1 to the optimum value in the apparatus configured as described above will be explained using a transmission voltage optimization flowchart in FIG. 2.

First, in step #1, the system control unit 9 sends to the transmitting and receiving unit 3 an instruction to cause the ultrasonic probe 1 to transmit an ultrasonic beam at the maximum transmission voltage E in the acoustic power limit range. The transmitting and receiving unit 3 applies the transmission voltage E of a specific transmission waveform to the individual vibrators of the ultrasonic probe 1 in such a manner that there is a delay between the vibrators. Being in contact with the subject 2, such as a biological body, the ultrasonic probe 1 scans the inside of the subject 2 with an ultrasonic beam. The ultrasonic probe 1 receives the reflected wave from, for example, a target region inside the subject 2 and outputs its echo signal. At the same time that scanning is done with the ultrasonic beam from the ultrasonic probe 1, the transmitting and receiving unit 3 adds the echo signals output from the individual vibrators of the ultrasonic probe 1 by introducing a delay in receiving.

The signal processing unit 4 subjects the output signal of the transmitting and receiving unit 3 to various processes, including a gain process, a phase detection process, an LPF process, a LOG compression process, and an image filtering process and outputs the result of these processes as subject data.

On the basis of the output data of the signal processing unit 4, the display processing unit 5 constructs either two- or three-dimensional image data or both, carries out a post-process, such as a dynamic range process, and displays either two- or three-dimensional ultrasonic image data or both on the display unit 7. The display processing unit 5 stores either the constructed two- or three-dimensional ultrasonic image data or both in the image memory 8.

Next, in step #2, the system control unit 9 sends an instruction to turn off the transmission voltage E (transmission voltage E=0) to the transmitting and receiving unit 3. This prevents the ultrasonic probe 1 from transmitting the ultrasonic beam.

In this state, the signal processing unit 4 subjects the output signal of the transmitting and receiving unit 3 to various processes, including a gain process, a phase detection process, an LPF process, a LOG compression process, and an image filtering process and outputs the result of these processes. The output data from the signal processing unit 4 is input to the histogram analysis unit 12, which collects the output data as noise data.

Next, in step #3, the subject data output from the signal processing unit 4 is input to the histogram analysis unit 12. For example, as shown in FIG. 3, the histogram analysis unit 12 sets samples m (e.g., the numbers of pixels) in the subject data in the direction of depth in which the ultrasonic probe 1 transmits an ultrasonic beam to the inside of the subject 2. At the same time, the histogram analysis unit 12 sets rasters n (e.g., the number of pixels) in the scanning direction of the ultrasonic beam.

The histogram analysis unit 12 sets a plurality of image areas each composed of samples m and rasters n (m×n pixels). One image area (m×n) is, for example, 4×4 pixels.

The histogram analysis unit 12 calculates a variance value Vi of each luminance value in the subject data output from the signal processing unit 4 for each image area (m×n). At the same time, the histogram analysis unit 12 calculates an average value Si by performing an averaging process (LPF) on the individual luminance values in the output data of the signal processing unit 4 for each image area (m×n).

Next, in step #4, the histogram analysis unit 12 calculates an average value Ni by performing an averaging process (LPF) on the individual luminance values for each image area (m×n) in the noise data output from the signal processing unit 4 when the transmission voltage E to the ultrasonic probe 1 is turned off.

Next, the biomedical tissue identification computing unit 13 receives the variance value Vi of luminance values, average value Si, and average value Ni of the noise data for each image area (m×n) in the subject data obtained by the histogram analysis unit 12. The biomedical tissue identification computing unit 13 determines whether the image area is the subject 2 on the basis of the variance value Vi, average value Si, and average value Ni.

Specifically, the biomedical tissue identification computing unit 13 calculates the difference SNRi (=Si−Ni) between the average value Si of the subject data and the average value Ni of the noise data and sets the difference SNRi as sensitivity.

Next, in step #6, according to the conditions for determining whether the image area is the subject 2 shown in expressions 2 and 3, the biomedical tissue identification computing unit 13 determines for each image area (m×n) whether the image area is the subject 2, on the basis of the variance value Vi of the subject data and the sensitivity SNRi.

If the result of the determination has shown that the expressions SNRi>SNRmin and Vmin<Vi<Vmax are satisfied, the biomedical tissue identification computing unit 13 determines that the image area (m×n) is the subject 2.

In contrast, if the result of the determination has shown that the expressions SNRi>SNRmin and Vmin<Vi<Vmax are not satisfied for each image area (m×n), the biomedical tissue identification computing unit 13 determines that the image area (m×n) is not the subject 2. That is, the biomedical tissue identification computing unit 13 determines that an image area other than the one fulfilling the expressions SNRi>SNRmin and Vmin<Vi<Vmax is not the subject 2.

Figure 4:
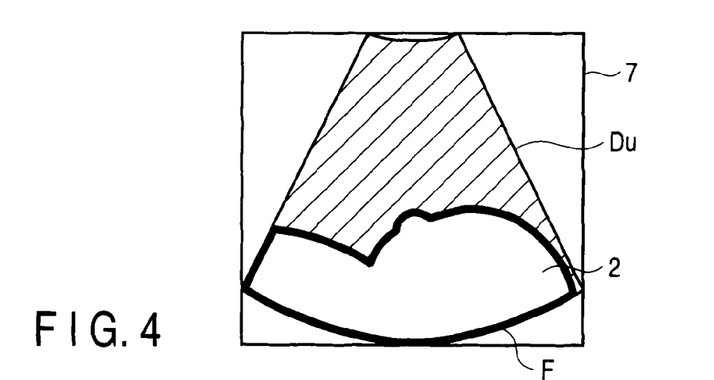
FIG. 4 shows a biological part determined to be a subject by a biomedical tissue identification computing unit in the apparatus of the embodiment.

FIG. 3 shows an ultrasonic image Du of the subject 2, such a biological body as an unborn baby, displayed on the display unit 7. FIG. 4 shows a biological part, such as an unborn baby, (inside a thick frame F) determined to be the subject 2 by a biomedical tissue identification computing unit 13. For example, if having determined the biological part F, such as an unborn baby, the biomedical tissue identification computing unit 13 can separate the biological part F from the ultrasonic image Du.

Next, in step #7, the optimum transmission voltage computing unit 14 calculates the average value SNRmean of sensitivities SNRi in each of the image areas (m×n) recognized as the subject 2 by the biomedical tissue identification computing unit 13, for example, in each of the image areas (m×n) in the inside of the biological part F determined to be a biological body, such as an unborn baby shown in FIG. 4.

Next, in step #8, the optimum transmission voltage computing unit 14 compares the average value SNRmean of sensitivities with the threshold value SNRtarget.

If the result of the comparison has shown that the average value SNRmean of sensitivities SNRi is greater than the threshold value SNRtarget, the optimum transmission voltage computing unit 14 calculates a transmission voltage E=Ea−ΔE lower than the transmission voltage E to the ultrasonic probe 2 by a voltage value ΔE corresponding to the difference between the average value SNRmin of sensitivities and the threshold value SNRtarget. The optimum transmission voltage computing unit 14 sends the transmission voltage E (=Ea−ΔE) to the system control unit 9.

In step #9, the system control unit 9 receives the transmission voltage E (=Ea−ΔE) found by the optimum transmission voltage computing unit 14 and feeds back the transmission voltage E to the transmitting and receiving unit 3. As a result, the transmission voltage E to the ultrasonic probe 2 drops by the voltage value ΔE corresponding to the difference the average value SNRmin of sensitivities and the threshold value SNRtarget.

The adjustment of the transmission voltage E to the ultrasonic probe 2 is made in real time. For example, the signal-to-noise ratio (the average value SNRmean of sensitivities SNRi) of the echo signal from the subject 2, a biological body, such as an unborn baby, is, for example, 30 dB or more at a minimum. If the signal-to-noise ratio minimum required for ultrasonic diagnosis of the subject 2 is defined as, for example, 10 dB, the acoustic power can be decreased by 20 dB. The signal-to-noise ratio of the echo signal from the subject 2 equal to or greater than 30 dB at a minimum is just an example and, needless to say, may take another value.

The timing with which the transmission voltage E to the ultrasonic probe 1 is limited may be at the time when the acoustic power adjustment switch 15 in the operation panel 11 is operated manually. For example, while looking at the ultrasonic image Du of the subject 2 displayed on the display unit 7 as shown in FIG. 3, the user operates the acoustic power adjustment switch 15. At this time, when being operated manually, the acoustic power adjustment switch 15 gives to the system control unit 9 an instruction to optimize the transmission voltage E to the ultrasonic probe 1.

The system control unit 9 executes step #1 to step #8 as described above, thereby giving an operation control instruction to each of the transmitting and receiving unit 3, signal processing unit 4, display processing unit 5, histogram analysis unit 12, biomedical tissue identification computing unit 13, and optimum transmission voltage computing unit 14. As a result, the average value SNRmean of sensitivities SNRi in each of the image areas (m×n) recognized as the subject 2 is calculated. If the average value SNRmean of sensitivities SNRi is greater than the threshold value SNRtarget, the transmission voltage E to the ultrasonic probe 1 is limited according to the difference between the average value SNRmin of sensitivities and the threshold value SNRtarget.

As described above, with the embodiment, the average value SNRmean of sensitivities SNRi in each of the image areas (m×n) recognized as the subject 2 is calculated. If the average value SNRmean of sensitivities SNRi is greater than the threshold value SNRtarget, the transmission voltage E to the ultrasonic probe 1 is limited according to the difference between the sensitivity average value SNRmin to the ultrasonic probe 1 and the threshold value SNRtarget. This enables the transmission voltage E sent to the ultrasonic probe 1 according to the subject to be adjusted automatically to the optimum value.

When the subject 2, a biological body, such as an unborn baby, is diagnosed, the acoustic power of the ultrasonic beam has to be limited for the regions of the subject 2 which need no diagnosis. Under such conditions, the embodiment can optimize the acoustic power of the ultrasonic beam to the subject 2 by adjusting the acoustic power of the ultrasonic beam automatically to the optimum acoustic power in an acoustic power limit range for the inside of the biological region F of an unborn baby or the like shown in, for example, FIG. 4. This prevents the throughput of the diagnosis of a plurality of diagnostic regions of, for example, the subject 2 from decreasing. The total time required to diagnose a plurality of diagnostic regions of the subject 2 can be shortened. Consequently, the irradiation time of the ultrasonic beam to the subject 2 can be made shorter.

Hereinafter, another embodiment of the invention will be explained.

In the above embodiment, the optimum transmission voltage computing unit 14 may calculate sensitivity SNRi each time a scan is done with the ultrasonic beam transmitted from the ultrasonic probe 1 and limit the transmission voltage E to the ultrasonic probe 1 on the basis of the sensitivity SNRi and a preset threshold value SNRtarget. In this case, too, as described above, the average value SNRmean of sensitivities SNRi in each of the image areas (m×n) recognized as the subject 2 is calculated. If the average value SNRmean of sensitivities SNRi is greater than the threshold value SNRtarget, the transmission voltage E to the ultrasonic probe 1 is limited according to the difference between the average value SNRmin of sensitivities and the threshold value SNRtarget.

Figure 5:
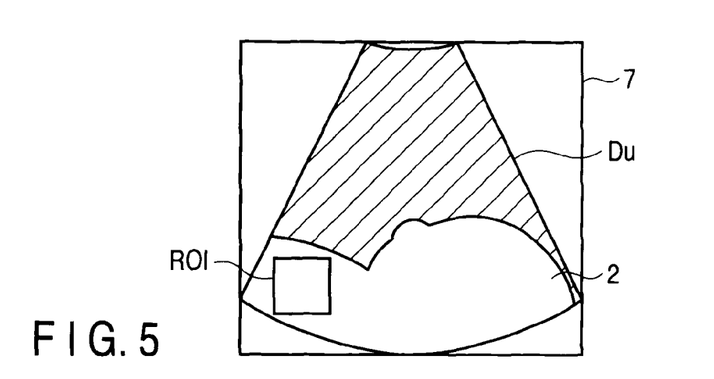
FIG. 5 shows a region of interest set in an ultrasonic image by the apparatus of the embodiment.

Moreover, for example, a region of interest ROI may be set in an ultrasonic image Du of the subject 2, such as a biological body shown in FIG. 5. In this case, the optimum transmission voltage computing unit 14 can set a threshold value SNRtarget inside and outside the region of interest ROI separately. Setting the threshold value SNRtarget inside and outside the region of interest separately makes it possible to transmit to the subject 2 an ultrasonic beam of the optimum acoustic power in the acoustic power limit range. An ultrasonic beam of needlessly high acoustic power is not transmitted to the parts other than the subject 2.

While in the above embodiment, the optimum transmission voltage computing unit 14 limits the transmission voltage E to the ultrasonic probe 1 in real time, the invention is not limited to this. For example, the optimum transmission voltage computing unit 14 may limit the transmission voltage E at regular intervals of time.

Figure 6:
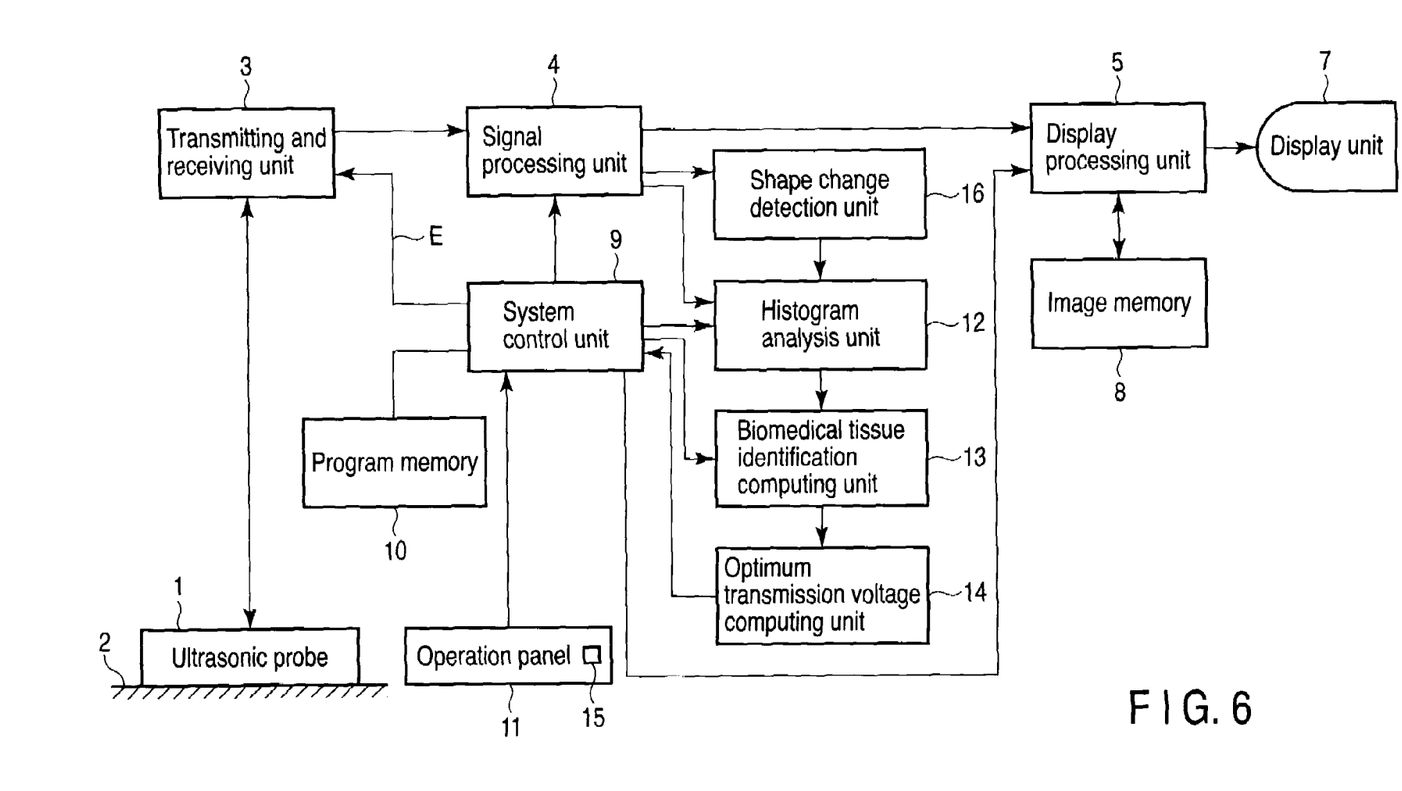
FIG. 6 is a block diagram showing the configuration of an ultrasonic diagnostic apparatus according to another embodiment of the invention.

Moreover, another embodiment of the invention is such that a shape change detection unit 16 is provided as shown in, for example, in FIG. 6. The shape change detection unit 16 detects a change in the shape of the subject 2 from the subject data output from the signal processing unit 4, that is, ultrasonic image data. The ultrasonic image data is composed of a plurality of temporally-consecutive frame images.

Accordingly, the shape change detection unit 16 compares two temporally-consecutive ones of the frame images in the ultrasonic image data and detects a change in the shape of the subject 2 from the result of the comparison. A change in the subject 2 includes a movement of the subject 2, a biological body, such as an unborn baby, a movement of the region causing the ultrasonic probe 1 to make contact with the subject 2, and a change in the angle at which the ultrasonic probe 1 is caused to make contact with the subject 2, or a change in the angle of the ultrasonic beam transmitted to the subject 2.

When the shape change detection unit 26 has detected a change in the shape of the subject 2, the histogram analysis unit 12 calculates not only a variance value Vi of each luminance value in the subject data for each image area (m×n pixels) but also an average value Si as described above. Moreover, the histogram analysis unit 12 calculates an average value Ni by performing an averaging process (LPF) on the individual luminance values for each image area (m×n) in the noise data when the transmission voltage E to the ultrasonic probe 1 is turned off.

Next, the biomedical tissue identification computing unit 13 determines whether the image area is the subject 2 on the basis of the variance value Vi, average value Si, and average value Ni.

Next, the optimum transmission voltage computing unit 14 calculates the average value SNRmean of sensitivities SNRi in each of the image areas (m×n) recognized as the subject 2 by the biomedical tissue identification computing unit 13, for example, in each of the image areas (m×n) in the inside of the biological part (or inside of a thick frame F) determined to be a biological body, such as an unborn baby shown in FIG. 4. The optimum transmission voltage computing unit 14 compares the average value SNRmean of sensitivities with the threshold value SNRtarget.

If the result of the comparison has shown that the average value SNRmean of sensitivities SNRi is greater than the threshold value SNRtarget, the optimum transmission voltage computing unit 14 calculates a transmission voltage E=Ea−ΔE lower than the transmission voltage E to the ultrasonic probe 2 by a voltage value ΔE corresponding to the difference between the average value SNRmin of sensitivities and the threshold value SNRtarget. The optimum transmission voltage computing unit 14 sends the transmission voltage E (=Ea−ΔE) to the system control unit 9.

With such another embodiment, when the shape of the subject 2 has changed, for example, when the subject 2, a biological body, such as an unborn baby, moves, the region causing the ultrasonic probe 1 to make contact with the subject 2 moves, or when the angle at which the ultrasonic probe 1 is caused to make contact with the subject 2 or the angle at which the ultrasonic beam transmitted to the subject 2 changes, the transmission voltage E sent to the ultrasonic probe 1 can be adjusted according to the subject 2 as in the above embodiment.

This invention is not limited to the above embodiments and may be embodied by modifying the component elements without departing from the spirit or essential character thereof. In addition, various inventions may be formed by combining suitably a plurality of component elements disclosed in the embodiments. For example, some components may be removed from all of the component elements constituting the embodiments. Furthermore, component elements used in different embodiments may be combined suitably.

What is claimed is:

1. An ultrasonic diagnostic apparatus comprising:
   an ultrasonic probe;
   a transmitting and receiving unit which transmits a voltage to the ultrasonic probe to cause the ultrasonic probe to transmit an ultrasonic beam and to receive an echo from a subject with the ultrasonic probe;
   a signal processing unit which acquires ultrasonic image data on the subject from an output signal of the transmitting and receiving unit;
   a subject recognition unit which sets a plurality of image areas in an image of the subject in the ultrasonic image data acquired by the signal processing unit, calculates a spatial variance value and a first spatial average value of a luminance value of the ultrasonic image data, and a second spatial average value of noise data for each of the image areas, and recognizes whether each of the image areas is a part of the image of the subject based on the spatial variance value, the first spatial average value, and the second spatial average value; and
   an optimum voltage computing unit that calculates a sensitivity, which is a difference between the first spatial average value and the second spatial average value, in the image area recognized as the subject by the subject recognition unit, and limits the transmission voltage to the ultrasonic probe based on the sensitivity and a preset threshold value; and
   a shape change detection unit which detects a change in shape of the subject from temporally-consecutive image data in the ultrasonic image data;
   wherein the optimum voltage computing unit calculates the sensitivity for each of the image areas recognized by the subject recognition unit when the shape change detection unit detects a change in shape of the subject, and limits the transmission voltage to the ultrasonic probe based on the sensitivity and the preset threshold value.

2. The ultrasonic diagnostic apparatus according to claim 1, wherein the optimum voltage computing unit calculates an average value of sensitivities in the image area, compares the average value of sensitivities with the threshold value, and if the average value of sensitivities is greater than the threshold value, lowers the transmission voltage to the ultrasonic probe.

3. The ultrasonic diagnostic apparatus according to claim 2, wherein the optimum voltage computing unit lowers the transmission voltage by a voltage value corresponding to the difference between the average value of sensitivities and the threshold value.

4. The ultrasonic diagnostic apparatus according to claim 1, wherein the optimum voltage computing unit calculates the sensitivity each time a scan is made with the ultrasonic beam transmitted from the ultrasonic probe and, on the basis of the sensitivity and the preset threshold value, limits the transmission voltage to the ultrasonic probe.

5. The ultrasonic diagnostic apparatus according to claim 1, wherein the optimum voltage computing unit is capable of setting the preset threshold value separately inside and outside a region of interest set in the subject.

6. The ultrasonic diagnostic apparatus according to claim 1, wherein the optimum voltage computing unit limits the transmission voltage to the ultrasonic probe in real time or at regular intervals of time.

7. The ultrasonic diagnostic apparatus according to claim 1, further comprising:
an optimization specifying unit which is for giving an instruction to optimize the transmission voltage to the ultrasonic probe
wherein the optimum voltage computing unit, when receiving an instruction from the optimization specifying unit, calculates a sensitivity in the image area recognized by the subject recognition unit and, on the basis of the sensitivity and the preset threshold value, limits the transmission voltage to the ultrasonic probe.

8. The ultrasonic diagnostic apparatus according to claim 7, wherein the optimization specifying unit has a switch which is operated manually to give the instruction to the optimum voltage computing unit.

9. The ultrasonic diagnostic apparatus according to claim 1, wherein the ultrasonic image data is composed of a plurality of temporally-consecutive frame images, and
the shape change detection unit compares temporally-consecutive ones of the frame images in the ultrasonic image data, thereby detecting a change in the shape of the subject.

10. An ultrasonic diagnostic method comprising:
transmitting a voltage to an ultrasonic probe to cause the ultrasonic probe to transmit an ultrasonic beam;
receiving an echo from a subject with the ultrasonic probe;
acquiring ultrasonic image data on the subject with a signal processing unit from an output signal of the ultrasonic probe;
setting a plurality of image areas in an image of the subject in the ultrasonic image data acquired by the signal processing unit, calculating a spatial variance value and a first spatial average value of a luminance value of the ultrasonic image data, and a second spatial average value of noise data for each of the image areas, and recognizing whether each of the image areas is a part of the image of the subject based on the spatial variance value, the first spatial average value, and the second spatial average value; and
calculating a sensitivity, which is a difference between the first spatial average value and the second spatial average value, in the image area recognized as the subject, and limiting the transmission voltage to the ultrasonic probe based on the sensitivity and a preset threshold value; and
detecting a change in shape of the subject from temporally-consecutive image data in the ultrasonic image data;
wherein the calculating calculates the sensitivity for each of the recognized image areas when the detecting a change in shape detects a change in shape of the subject, and limits the transmission voltage to the ultrasonic probe based on the sensitivity and the preset threshold value.

11. The ultrasonic diagnostic method according to claim 10, wherein the limiting the transmission voltage to the ultrasonic probe includes:
calculating an average value of sensitivities in the image area,
comparing the average value of sensitivities and the threshold value, and
if the average value of sensitivities is greater than the threshold value, lowering the transmission voltage by a voltage value corresponding to the difference between the average value of sensitivities and the threshold value.

* * * * *